US010946376B2

(12) United States Patent
Weber et al.

(10) Patent No.: US 10,946,376 B2
(45) Date of Patent: Mar. 16, 2021

(54) CARRIER ELEMENT FOR INTRODUCING A DRY SUBSTANCE INTO A FLOW CELL

(71) Applicant: THINXXS MICROTECHNOLOGY AG, Zweibrücken (DE)

(72) Inventors: Lutz Weber, Zweibrücken (DE); Tina Röser, Brohl (DE)

(73) Assignee: THINXXS MICROTECHNOLOGY AG, Zweibrücken (DE)

( * ) Notice: Subject to any disclaimer, the term of this patent is extended or adjusted under 35 U.S.C. 154(b) by 30 days.

(21) Appl. No.: 16/265,127

(22) Filed: Feb. 1, 2019

(65) Prior Publication Data

US 2019/0224673 A1 Jul. 25, 2019

Related U.S. Application Data

(63) Continuation-in-part of application No. 14/902,787, filed as application No. PCT/EP2014/064290 on Jul. 4, 2014, now Pat. No. 10,232,367.

(30) Foreign Application Priority Data

Jul. 5, 2013 (EP) .................................... 13175335

(51) Int. Cl.

*B01L 3/00* (2006.01)
*G01N 35/00* (2006.01)
*G01N 33/48* (2006.01)
*G01N 15/06* (2006.01)
*G01N 33/00* (2006.01)
(Continued)

(52) U.S. Cl.

CPC ........... *B01L 3/502715* (2013.01); *B01L 3/52* (2013.01); *B01L 2200/0689* (2013.01); *B01L 2200/16* (2013.01); *B01L 2300/042* (2013.01); *B01L 2300/0816* (2013.01); *B01L 2300/0848* (2013.01); *B01L 2300/12* (2013.01); *B01L 2300/123* (2013.01)

(58) Field of Classification Search

CPC ........ B01L 3/00; B01L 3/502715; B01L 3/52; G01N 35/00; G01N 33/48; G01N 15/06; G01N 33/00; G01N 21/75; G01N 31/22; G01N 33/52

USPC ...... 422/502, 503, 68.1, 406, 411, 418, 419, 422/420; 436/43

See application file for complete search history.

(56) References Cited

U.S. PATENT DOCUMENTS 4,604,360 A * 8/1986 Hounsell ................ C12M 45/22 422/236
7,595,871 B2 9/2009 Weber
(Continued)

FOREIGN PATENT DOCUMENTS

DE 102006021364 A1 6/2009
EP 0733714 A1 9/1996
(Continued)

*Primary Examiner* — Brian J. Sines
(74) *Attorney, Agent, or Firm* — Lucas & Mercanti, LLP; Klaus P. Stoffel

(57) ABSTRACT

A carrier element for introducing a dry substance into a cavity of a microfluidic flow cell or a chamber or cavities for interacting with a fluid, including: a plug-like body figure to be insertable into a passage of the flow cell leading to the cavity; and, a carder surface for receiving the drive substance, the carder surface being at an end of the body facing the cavity when the body is inserted in the passage.

13 Claims, 4 Drawing Sheets

(51) Int. Cl.
*G01N 31/22* (2006.01)
*G01N 33/52* (2006.01)

(56) References Cited

U.S. PATENT DOCUMENTS

| | | | | |
|---|---|---|---|---|
| 8,088,576 | B2 | 1/2012 | Gumbrecht et al. | |
| 8,790,932 | B2 | 7/2014 | Augstein et al. | |
| 2006/0094028 | A1* | 5/2006 | Danna | B01L 3/502715 435/6.11 |
| 2006/0115805 | A1* | 6/2006 | Hansen | A61F 13/38 435/4 |
| 2007/0255175 | A1* | 11/2007 | Sangha | A61B 10/02 600/572 |
| 2008/0193926 | A1* | 8/2008 | Abraham-Fuchs | A61B 10/0051 435/6.14 |
| 2009/0215159 | A1* | 8/2009 | Kirby | A61B 10/0096 435/287.2 |
| 2009/0286225 | A1* | 11/2009 | Wheeler | C12Q 1/04 435/5 |
| 2010/0274155 | A1* | 10/2010 | Battrell | A61B 10/0096 600/572 |
| 2011/0004122 | A1* | 1/2011 | Sangha | G01N 1/02 600/572 |
| 2011/0143365 | A1* | 6/2011 | Buchanan | B01L 3/5029 435/7.1 |
| 2011/0171754 | A1* | 7/2011 | Redmond | B01L 3/502715 436/518 |
| 2012/0196767 | A1 | 8/2012 | Cooney et al. | |
| 2013/0130262 | A1 | 5/2013 | Battrell | |
| 2014/0072960 | A1* | 3/2014 | Lansing | G01N 33/5302 435/5 |
| 2015/0072362 | A1* | 3/2015 | Lui | A61B 10/0096 435/7.92 |
| 2015/0241319 | A1 | 8/2015 | Chiesl et al. | |
| 2017/0241949 | A1* | 8/2017 | Bort | B01F 13/0071 |
| 2018/0017548 | A1 | 1/2018 | Pang | |

FOREIGN PATENT DOCUMENTS

| | | | |
|---|---|---|---|
| EP | 1418233 | A1 | 5/2004 |
| EP | 2198964 | B1 | 6/2010 |
| EP | 2610009 | A1 | 7/2013 |
| WO | 2005106024 | A1 | 11/2005 |
| WO | 2008134462 | A1 | 11/2008 |
| WO | 2010005197 | A2 | 1/2010 |
| WO | 2011051735 | A2 | 5/2011 |
| WO | 2012154306 | A1 | 11/2012 |

* cited by examiner

CARRIER ELEMENT FOR INTRODUCING A DRY SUBSTANCE INTO A FLOW CELL

CROSS-REFERENCE TO RELATED APPLICATIONS

The present application is a Continuation-In-Part Application of U.S. patent application Ser. No. 14/902,787, filed Jan. 4, 2016, which is a 371 of International application PCT/EP2014/064290, filed Jul. 4, 2014, which claims priority of EP 13 175 335.2, filed Jul. 5, 2013, the priority of these applications is hereby claimed and these applications are incorporated herein by reference.

BACKGROUND OF THE INVENTION

The invention pertains to a microfluidic flow cell with a dry substance arranged in a cavity inside the flow cell for interaction with a fluid present in the cavity.

Microfluidic flow cells, which are being used increasingly as “minilabs” for the analysis and/or synthesis of fluids, especially in the field of diagnostics, contain reactive substances in liquid and/or solid form, which are introduced into the flow cells during the production of the cells. To introduce a dry reagent, one of the assembly steps involves applying a reagent liquid, that is, a carrier liquid in which a reagent is dissolved or suspended and which is later to be dried, to the area intended to hold the dry reagent inside the flow cell, e.g., a channel or a chamber, while that area is still accessible. After that, the entire flow cell component, only part of which has been wetted with the reagent, is subjected to a drying process before the further assembly steps are carried out; this drying step is often associated with a heat treatment to accelerate the process, or it takes the form of a freeze-drying process to protect the reagents and ensure the stability and resuspendability properties. The disadvantage is that the component, the dimensions of which usually far exceed those of the area to be dried, takes up a great deal of space in a drying chamber. In addition, the drying treatment can impair this flow cell component itself, especially the sensitive components mounted on it. Above all, the dry substance which has formed can be subject to degradation during the course of the final assembly of the flow cell, in particular through contact with air, atmospheric humidity, and welding heat or through the influence of the adhesives used during assembly, which are used in many cases hermetically to seal the corresponding channel areas of a microfluidic flow cell. A method for introducing a dry substance into a flow cell as described above is explained in, for example, EP 2 198 964 B1.

SUMMARY OF THE INVENTION

The invention is based on the goal of creating a new microfluidic flow cell of the type described above with an integrated dry substance, which cell can be produced more easily than the prior art allows without the assembly environment causing any impairment to the dry substance or to any other of the components of the flow cell.

The flow cell according to the invention which achieves this goal is characterized in that a passage leads into the cavity, and in that a carrier element, which can be inserted into the passage is provided, this carrier element having a carrier surface which faces the cavity and holds the dry substance.

It is advantageous for the dry substance to be obtained by drying a reagent liquid on a carrier element separate from the entire rest of the flow cell, this carrier element serving solely to hold the dry substance, which thus makes it possible to introduce the dry substance into the flow cell in a subsequent assembly step. The risk of impairment to the components of the flow cell by the drying process and the risk of impairment to the introduced dry reagent by additional assembly work on the flow cell are eliminated. The carrier element can be much smaller than the flow cell, wherein the dimensions of the carrier element are oriented around the size of the area intended to carry the dry reagent. Coatings which promote the adhesion of the dry substance to its carrier surface can advantageously remain limited to the carrier surface of the carrier element, so that such coatings cannot, negatively affect the welds or adhesive bonds.

It Is obvious that the cavity can form a channel network for the transport, analysis, and/or synthesis of a fluid. Several carrier elements, possibly with different dry substances, can be introduced into the flow cell.

In one embodiment of the invention, the cavity is bounded by a recess in a preferably plate-shaped substrate and by a preferably film-like cover, which seals the recess; and the passage is formed in the substrate, which is thicker than the film-like cover.

It is obvious that the passage will advisably extend to an external surface of the flow cell, so that the dry substance can be introduced into the flow cell during a last assembly step of the production process.

The carrier element is preferably shaped in such a way that it can be connected detachably and/or undetachably to the flow cell to seal off the cavity. The shape of the passage is preferably adapted to the shape of the carrier element. Leak-tightness can be achieved in particular by welding and/or adhesively bonding the carrier element into the passage, or possibly mechanically by pressing it into the passage.

Accordingly, the carrier element advisably fills the passage completely, i.e., at least the complete cross section of the passage, wherein the carrier element and the passage preferably both have a circular cross section, which is advantageous in terms of fabrication.

In a further elaboration of the invention, the carrier element tapers down toward the cavity as the passage becomes narrower. In particular, it is therefore possible, simply by pressing the carrier element mechanically into the passage, to achieve a tight seal of the cavity in the manner of a press-fit.

The carrier element preferably comprises a section which projects outwardly from the flow cell, which section can serve as a gripping part for facilitating manual handling or automated assembly.

The projecting section can extend beyond the external surface of the flow cell in the form of a collar, wherein the collar can also serve to provide an additional sealing function for the cavity.

In another embodiment, the carrier element can be screwed into the passage.

The carrier surface of the carrier element can be flush with, or offset from, the adjacent wall surface of the cavity. Alternatively, the carrier element can project beyond the adjacent wall surfaces of the cavity.

The carrier surface advisably comprises a structuring, a coating, and/or a surface modification which promotes the adhesion of the dry substance.

The carrier element and the carrier surface carrying the dry reagent consist preferably of plastic. Alternatively, the carrier surface can be made of a separate surface component of glass, silicon, ceramic, or metal, which is connected to the rest of the carrier element and which is applied by means of welding or adhesive bonding. This is advantageous when the surface required for the application of the dry reagent cannot be realized by means of a plastic surface or a coating.

The dry reagents which can be used include salts, buffers for, e.g., cell lysis, magnetic and non-magnetic beads, enzymes, antibodies, DNA fragments, proteins, and PCR reagents, or alternatively even cells.

The invention is explained in greater detail below on the basis of exemplary embodiments and the attached drawings, which refer to these exemplary embodiments.

DETAILED DESCRIPTION OF THE INVENTION

Figure 1:
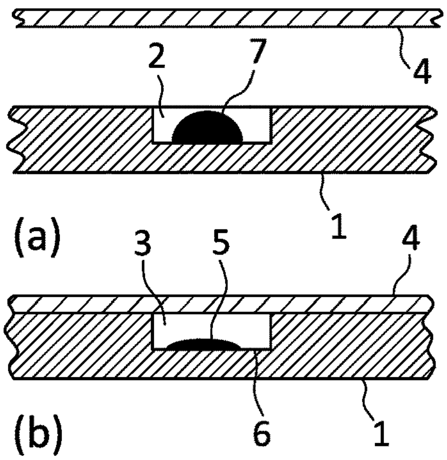
FIG. 1 (PRIOR ART)
FIG. 1 shows a diagram explaining the production of flow cells with integrated dry substance according to the prior art.

A flow cell, part of which is shown in FIG. 1, comprises a plate-shaped substrate 1 with a recess 2, which is covered to form a cavity 3 by a film 4, which is adhesively bonded and/or welded to the substrate. The cavity 3 is part of a channel network of the flow cell (the rest of which not being shown in FIG. 1); in particular, it forms a channel area in which a dry reagent 5 comprising antibodies, for example, adheres to a channel wall 6.

The dry reagent 5 originates from a reagent liquid 7, which is dispensed into the recess 2 forming a channel or chamber area of the flow cell before the recess 2 is sealed by the film 4. To obtain the dry reagent 5 from the reagent liquid 7, the entire substrate 1 is subjected to a heat treatment and/or a freeze-drying process.

Figure 2:
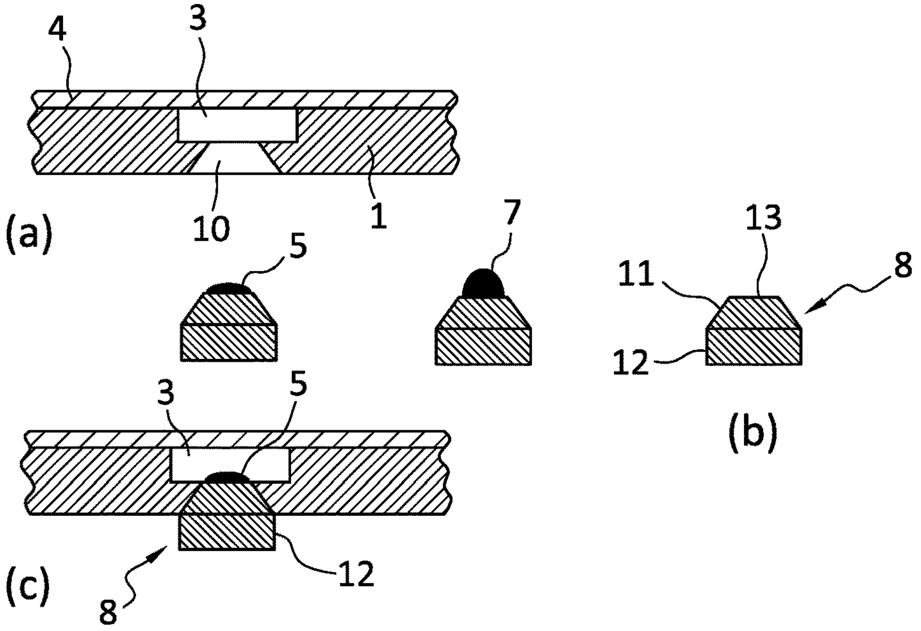
FIG. 2 shows a diagram explaining the production of a flow cell according to the invention.

FIG. 2 shows a method for introducing a dry substance, especially a dry reagent 5, into a flow cell, in which the dry reagent 5 is applied to a separate carrier part 8. A cavity 3 in a flow cell, which can be, for example, an area of the channel 9 shown in FIG. 3, comprises a through-opening 10, into which the conical section 11 of the carrier element 8, comprising a carrier surface 13 for the dry reagent 5, can be inserted to form a liquid-tight seal of the cavity 3. The carrier element eight can be plug-like body that it is insertable into the passage of the flow cell leading to the cavity. After assembly, the carrier surface 13 forms a part of the wall surface of the cavity 3. A fluid transported or processed in the cavity 3 can thus enter into interaction with the dry reagent; in particular, the dry reagent can be dissolved by the fluid and resuspended. It is also possible for components of the fluid such as cells or analytes to interact with and/or to bind to the dry reagent as the fluid flows over the carrier surface, possibly several times in different transport directions.

The carrier element 8 fitted into the through-opening 10 can be adhesively bonded or welded to the substrate. A section 12 of the carrier 8 which extends beyond the through-opening 10 on the side of the substrate 1 facing away from the cavity 3 serves as a gripping part, which facilitates the assembly of the carrier element 8.

In contrast to the example of FIG. 1 pertaining to the prior art, it is not necessary to expose the entire substrate 1, as in the example of FIG. 1, to a drying action to obtain the dry reagent 5 from the reagent liquid 7. On the contrary, only the carrier element 8 must be given a drying treatment, which saves space in the drying chamber. The main components of the flow cell, i.e., the substrate 1 and the film 4, are not subjected to any stress through the drying process, and, because the dry substance 5 is introduced into the flow cell after the steps required to fabricate the cell, in particular the welding of the film 4 to the substrate 1, the dry substance suffers no degradation.

Figure 3:
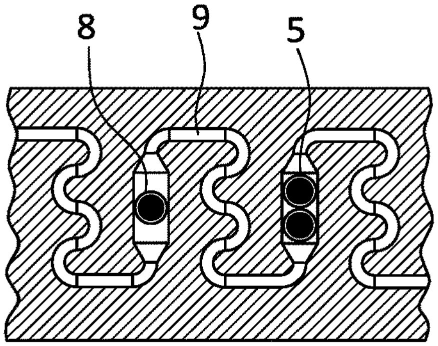
FIG. 3 shows a detailed view of the flow cell according to FIG. 2.

As FIG. 3 shows, several openings for the acceptance of carrier elements 8, possibly with different dry reagents 5 applied to them, can be present in the channel 9. In the example of FIG. 3, the meander-shaped channel 9 serves to re-dissolve the dry reagents 5 introduced by the carrier elements 8 as the liquid flows over them in different directions.

The substrate 1 and the film 4 of the flow cell preferably consist of a plastic, both of them especially of the same plastic, wherein PMMA, PC, PS, PEEK, PP, PE, COC, and COP, for example, can be considered. The carrier element 8 is also preferably a plastic part, which consists in particular of the same plastic as the substrate. The plastic substrate and the plastic carrier element are advisably produced by injection-molding.

Figure 4:
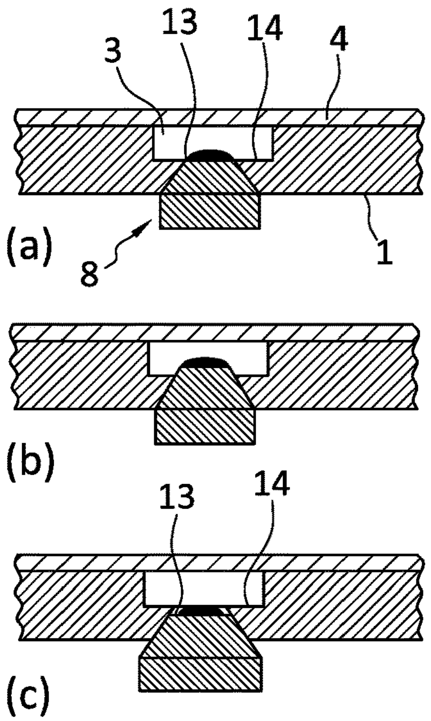
FIG. 4 shows exemplary embodiments of the arrangement of a carrier surface of a carrier element inside a cavity of a flow cell.

As can be derived from FIG. 4, the carrier surface 13 of the carrier element 8 holding the dry reagent 5 can be flush with, or set back from, the adjacent wall surface 14 of the cavity 3. According to FIG. 4*b*, the carrier surface 13 of the carrier element 8 can also project into the cavity 3. This can be advantageous for the purpose of producing local turbulence in a laminar flow, usually present in microchannels, by providing an abrupt change in the channel cross section and/or for the purpose of increasing the flow velocity of the fluid to accelerate and control the redissolution of the dry reagent, for example, by reducing the cross section of the channel in the area where the carrier element 8 has been introduced. There is also the advantage that, when the introduction of the carrier elements 8 is automated, it is possible to compensate for manufacturing tolerances of the components.

Figure 5:
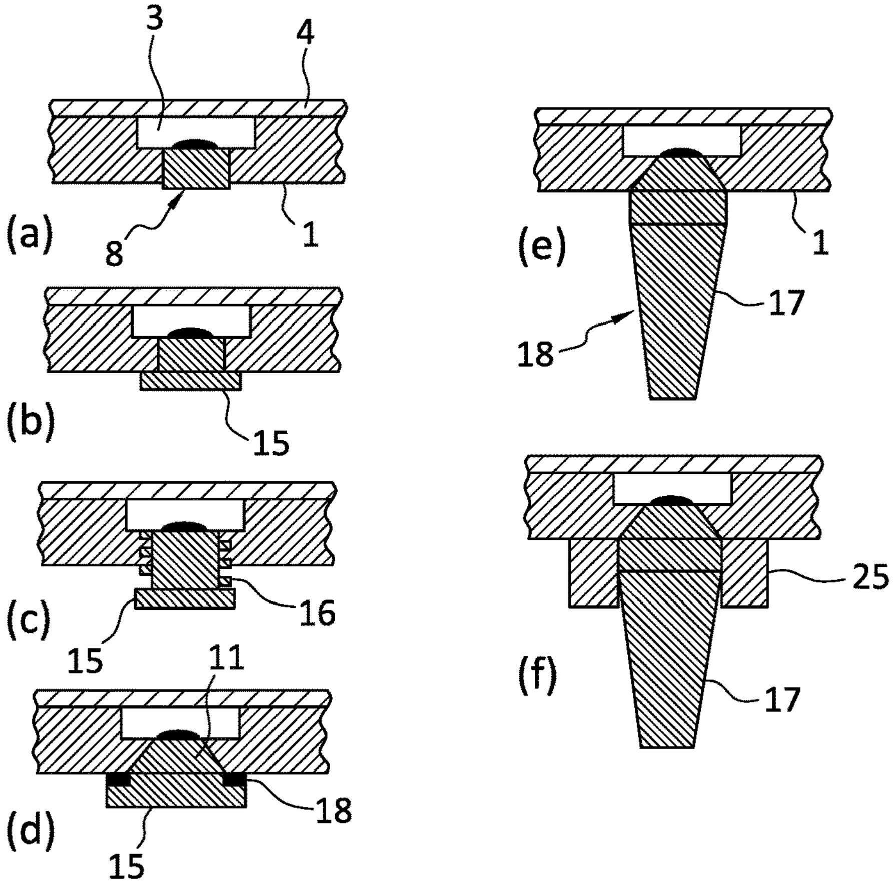
FIG. 5 shows addition& exemplary embodiments of carrier elements according to the invention.

FIG. 5 shows additional embodiments of carrier elements 8, which can be cylindrical as in FIG. 5*a* or cylindrical with a collar 15 resting against the substrate 1 from below as in FIG. 5*b*.

FIG. 5*c* shows an embodiment of a cylindrical carrier element 8 with a collar 13 and an external thread 16, which engages in an internal thread in the associated through-opening. In the case of the latter embodiment, the carrier element 8 advantageously can be detached from the flow cell, insofar as no other measures such as adhesive bonding or welding to the substrate 1 have been carried out in addition to the screw-in connection. This detachability can be advantageous when the dry reagent is to be removed from the flow cell and subjected to further analysis after it has interacted with the fluid.

A carrier element 8 which is detachable from the flow cell and which has an elongated gripping part 17 is shown in FIG. 5*e*. The carrier element 8 can be pressed into the associated through-opening in the substrate 1 to form a liquid-tight seal of the cavity 3.

The elevated edge 25 on the substrate 1 according to FIG. 5*f*, the thickness of which is typically in the range of 0.5-3 mm, makes it easier to guide the carrier element 8 into the opening.

FIG. 5*d* shows a carrier element 8 with a conical section and a collar 15 projecting beyond the through-opening; the collar is sealed off against the substrate 1 by a ring seal 18.

The rotationally symmetric carrier elements can comprise a marking, which makes it possible to introduce the carrier elements into the through-opening in the desired rotational position.

Figure 6:
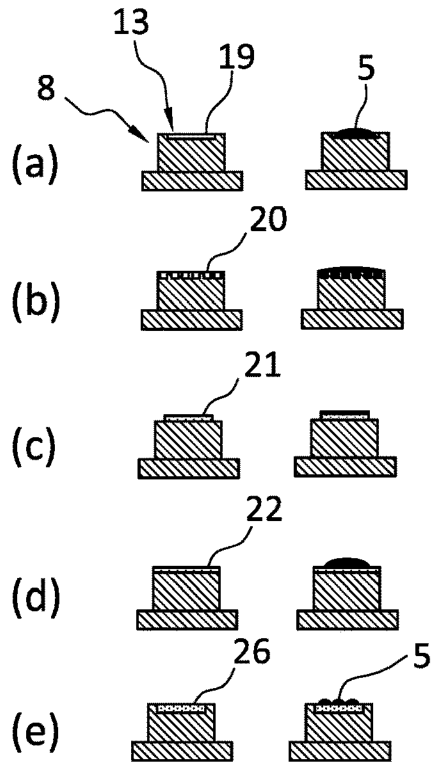
FIG. 6 shows exemplary embodiments of carrier surfaces of carrier elements.
Figure 7:
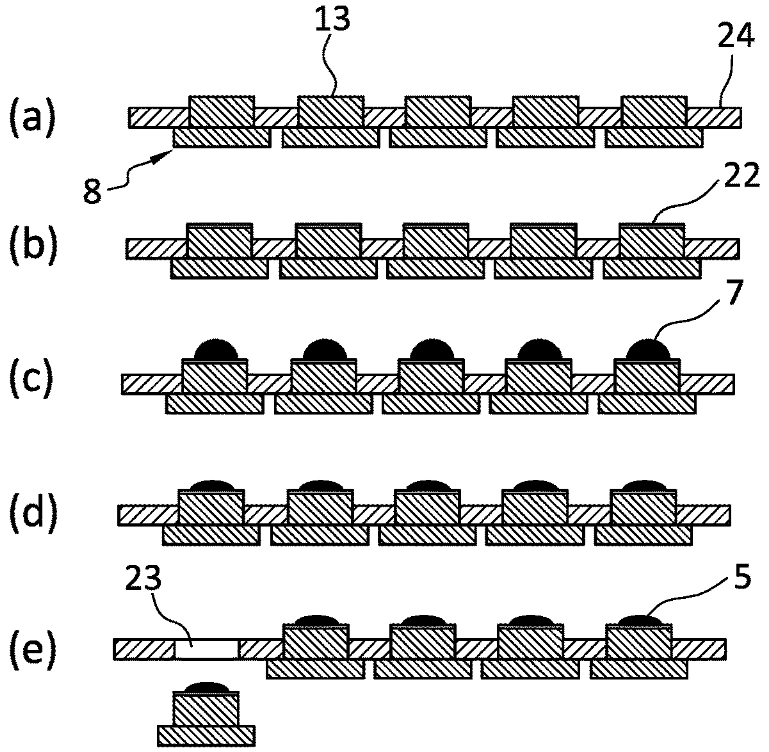
FIG. 7 shows a diagram explaining the application of a dry substance to the carrier elements.

FIG. 6 shows exemplary embodiments of carrier elements 8 with carrier surfaces 13 of various configurations, wherein FIG. 6*a* shows a carrier element with a depression 19 to hold a dry reagent 5. In the exemplary embodiment of FIG. 6*b*, a carrier surface 13 is provided with a plurality of retaining depressions in the form of grooves 20 arranged crosswise with typical cross-sectional dimensions ranging from 0.01×0.01 $mm^2$ to 1×1 $mm^2$ to hold a dry reagent. The advantage is that the surface of the carrier surface 13 can be easily increased in this way, so that either a larger amount of dry reagent 5 can be applied to a carrier element 8 of the same dimensions and/or the dry substance can be dried more homogeneously than is possible in the case of a large drop on a smooth carrier surface and/or the microstructure of the carrier surface 13 formed by the retaining depressions 20 can produce turbulence when the fluid flows over them, which positively affects the redissolution behavior. Alternatively, the grooves can also have the form of concentric circles, FIG. 6*c* shows a retaining surface with a porous element 21, applied to the carrier surface by clamping, adhesive bonding, or welding, in which a dry substance can be deposited. The advantage here is that the porous element 21 can provide an enlarged surface area for holding the dry reagent 5.

FIG. 6*d* shows a carrier element with a treated carrier surface, wherein the treatment can be, for example, a wet-chemical treatment, a plasma treatment, or a corona treatment. Alternatively, a treatment by means of plasma polymerization or the PVD process can lead to a coating 22, e.g., a glass or metal coating.

A carrier component shown in FIG. 6*e* is configured as two separate parts, one of which is a surface component 26. The surface component 25 forming the surface of the carrier consists of glass, silicon, or ceramic, for example, instead of preferably a plastic, out of which the rest of the carrier component is made. When the functionalization, i.e., the application of the dry reagent to the carrier surface, requires such materials as in the case of protein-based (e.g. antibody based) or nucleic acid-based analysis technologies, the amounts of these materials, which are often much more expensive than plastic, is advantageously decreased, since they occupy only a limited surface area, wherein dimensions ranging from 0.5×0.5 mm to 5×5 mm and thicknesses ranging from 0.1 to 1 mm can be considered. The surface component 26 can be fastened to the rest of the carrier component by clamping or by adhesive bonding or welding.

With respect to the application of the dry substance 5, a large number of carrier elements 8 can be processed simultaneously, in that the carrier elements 8, as shown in step 7*a*, are arranged on a carrier tablet 24 comprising rows of holes 23. In the next step 7*b* of the process, a layer 22, which improves the adhesion of a substance, is produced simultaneously on all carrier surfaces 13 of the carrier elements 8. The coating can also cover other surface areas of the carrier element 8 not intended for the application of the dry reagent 5. In steps 7*c* and 7*d* of the process, a reagent liquid 7 is applied to the layers 22, and then a drying treatment is carried out, so that the dry substance 5 is deposited on, and adheres to, the layers 22. Finally, in step 7*e*, the finished carrier elements 8 provided with a dry substance 5 are removed for processing.

Figure 8:
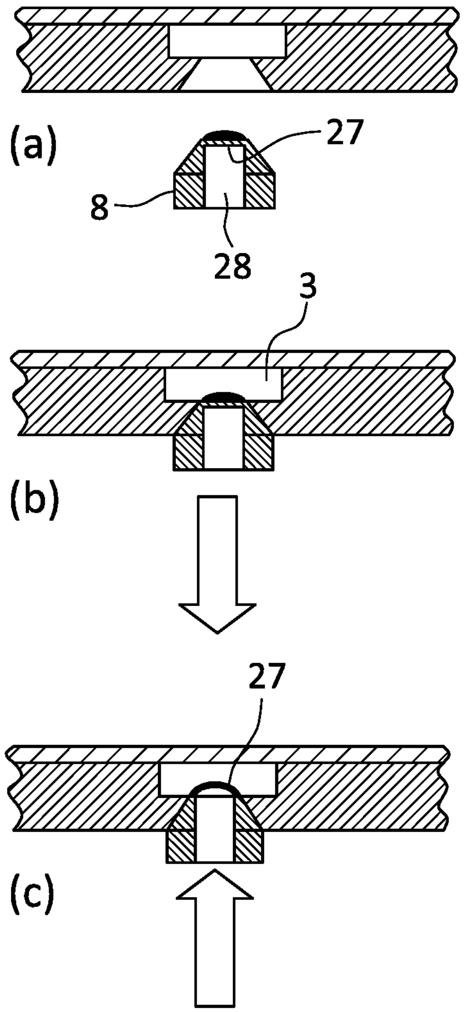
FIG. 8 shows another exemplary embodiment of a carrier element according to the invention.

Reference is now made to FIG. 8, where another exemplary embodiment of a carrier element 8 is shown.

The carrier element 8 comprises a carrier surface for a dry substance 5; the carrier surface is formed by a membrane, film or foil 27. The membrane can be an integral part of the rest of the carrier element 8, or it can be a separate component bonded to the rest of the carrier element, this separate component preferably consisting of the same plastic as the rest of the carrier element.

If the membrane or foil 27, which seals off one end of a through-opening 28 formed in the carrier element 8, is transparent, there is the possibility of monitoring the interaction of the fluid with the dry substance 5 by optical detection or optical detection means as shown in FIG. 8*b*.

In addition, as shown in FIG. 8*c*, there is the possibility of subjecting the membrane 27 to either pneumatic or mechanical pressure to give it a concave or convex shape. In particular through the alternating inward and outward bulging of the membrane 27, the interaction between the dry substance and the fluid can be stimulated, which improves the resuspension of dry substances and also the binding of components of the fluid to dry substances, e.g., in the case of antibodies.

The carrier surface can have a spherical or a spherical surface profile and/or a surface texture.

The dry substance in a hearing to the carrier surface becomes re-suspended when contacted with a fluid, or stays on the surface of the carrier and captures contents of the fluid that Is in contact with the substance.

The carrier surface for receiving the dry substance can carry multiple identical or different dry substances.

The invention claimed is:

1. A device for arranging a dry substance within a cavity of a microfluidic flow cell, the device comprising:

a plug-like carrier element; and a dry substance adhered to the carrier element, wherein the carrier element is a plastic injection-molded part and the dry substance is adhered to the carrier element by heat or freeze drying, the dry substance being adhered to plastic material of the carrier element directly or via an intermediate layer, wherein the plug-like carrier element has a cylindrical or conical body with a front surface that forms a carrier surface to which the dry substance is adhered, wherein the body is configured to be insertable into a passage of the flow cell leading to the cavity so that the carrier surface with the dry substance borders the cavity, wherein the cylindrical or conical body has a lateral surface configured to close the passage in a fluid-tight manner, wherein the conical body tapers toward the carrier surface and wherein a collar is arranged at an end of the cylindrical body opposite to the carrier surface.

2. The device according to claim 1, wherein the carrier element and the passage have a circular cross section.

3. The device according to claim 1, wherein the body is configured so that the end of the body opposite the carrier surface projects outward from the flow cell when the body is inserted into the passage.

4. The device according to claim 3, wherein the body is configured so that the collar is restable externally against the flow cell from below when the body is inserted into the passage.

5. The device according to claim 1, wherein the body is configured so that the carrier surface is flush with or set back from an adjacent wall surface of the cavity when the body is inserted into the passage, or so that the front surface of the body projects beyond the adjacent wall surface of the cavity into the cavity when the body is inserted into the passage.

6. The device according to claim 1, wherein the dry substance adheres to the carrier surface, and the carrier surface comprises a coating, and/or a surface modification that promotes the adhesion.

7. The device according to claim 1, wherein the carrier surface for the dry substance is formed on a surface of a separate component that is connected to a remainder of the carrier element and is of a material different from the remainder of the carrier element.

8. The device according to claim 1, wherein the carrier surface for the dry substance is formed by a membrane, film or foil that seals off a through-opening in the carrier element from the cavity.

9. The device according to claim 8, wherein the membrane or film is transparent to permit observation of an interaction between the dry substance in the fluid by optical detection means and/or elastically deformable by action exerted on the membrane through the through-opening.

10. The device according to claim 1, wherein the carrier surface comprises a spherical or a spherical surface profile and/or a surface texture.

11. The device according to claim 6, wherein the dry substance adhering to the carrier surface is re-suspended when contacted by the fluid or stays on the carrier surface and captures contents of the fluid in contact with the substance.

12. The device according to claim 1, wherein the carrier surface is configured to carry multiple identical or different dry substances.

13. The device according to claim 7, wherein the separate component is made of glass, silicon, metal or ceramic.

* * * * *